US006242009B1

(12) United States Patent
Batarseh et al.

(10) Patent No.: US 6,242,009 B1
(45) Date of Patent: Jun. 5, 2001

(54) MICROBICIDAL FORMULATIONS AND METHODS TO CONTROL MICROORGANISMS

(76) Inventors: Kareem I. Batarseh, 82 J Airport Blvd., Morgantown, WV (US) 26505; Marwan Al-Kayed, P.O. Box 413, Naour, Amman (JO)

( * ) Notice: Subject to any disclaimer, the term of this patent is extended or adjusted under 35 U.S.C. 154(b) by 0 days.

(21) Appl. No.: 09/294,143

(22) Filed: Apr. 20, 1999

(51) Int. Cl.[7] .......................... A01N 59/00; A01N 33/00
(52) U.S. Cl. ..................... 424/618; 424/613; 424/614; 424/616; 424/617; 424/620; 424/621; 424/622; 424/625; 424/626; 424/627; 424/629; 424/630; 424/638; 424/639; 424/644; 424/641; 424/646; 424/649; 424/650; 424/652; 424/654; 424/655; 424/682; 424/702; 514/492; 514/493; 514/494; 514/495; 514/497; 514/498; 514/499; 514/500; 514/501; 514/504; 514/505; 514/553; 514/554; 514/557; 514/561; 514/635; 514/706; 514/714; 514/724
(58) Field of Search ..................... 514/553, 554, 514/557, 561, 492, 493, 494, 495, 497, 498, 499, 500, 501, 504, 505, 706, 714, 724, 635; 424/617, 618, 620, 621, 622, 625, 626, 627, 629, 630, 638, 639, 644, 641, 646, 649, 650, 652, 654, 655, 682, 702, 613, 614, 616

(56) References Cited

U.S. PATENT DOCUMENTS

| | | |
|---|---|---|
| 3,422,183 | 1/1969 | Ellison ................................. 424/28 |
| 4,337,269 * | 6/1982 | Berke et al. ......................... 514/494 |
| 4,396,413 | 8/1983 | Miller et al. ............................. 71/67 |
| 4,425,325 | 1/1984 | Ritchey et al. ........................ 424/54 |
| 4,758,439 | 7/1988 | Godfrey ................................ 426/74 |
| 4,830,716 | 5/1989 | Ashmead ............................... 204/72 |
| 4,847,049 | 7/1989 | Yamamoto ............................ 422/24 |
| 4,915,955 | 4/1990 | Gomori ............................... 424/616 |
| 5,342,846 | 8/1994 | Singh et al. .......................... 514/312 |
| 5,389,360 | 2/1995 | Mobley et al. ........................ 424/49 |
| 5,504,055 | 4/1996 | Hsu ..................................... 504/121 |
| 5,510,315 | 4/1996 | Kurotsu et al. ...................... 504/115 |
| 5,516,480 | 5/1996 | Krall et al. ........................... 264/343 |
| 5,516,925 | 5/1996 | Pedersen et al. ...................... 556/50 |
| 5,616,251 | 4/1997 | Batarseh ............................. 210/725 |
| 5,708,023 * | 1/1998 | Modak et al. ........................ 514/494 |
| 5,710,252 | 1/1998 | Weber et al. ........................ 530/356 |

FOREIGN PATENT DOCUMENTS

| | | |
|---|---|---|
| 1 642 001 | 4/1971 | (DE) . |
| 0 041 792 * | 5/1981 | (EP) . |
| 2 728 143 | 12/1994 | (FR) . |
| 07138167 | 5/1995 | (JP) . |
| 2000-156611 | 1/1998 | (JP) . |
| 10338605 | 12/1998 | (JP) . |
| 11-209209 | 3/1999 | (JP) . |
| WO 94/04167 | 3/1994 | (WO) . |
| 95/13700 * | 5/1995 | (WO) . |
| WO 96/01231 | 1/1996 | (WO) . |
| WO 97/02038 | 1/1997 | (WO) . |
| 97/33477 * | 9/1997 | (WO) . |
| WO 99/17735 | 4/1999 | (WO) ......................... 7/22 |
| WO 00/27390 | 5/2000 | (WO) . |

OTHER PUBLICATIONS

Tzeng et al., "Products in light–mediated reactions of free methionine–riboflavin mixtures that are biocidal to microorganisims", (Can. J. Microbiol., vol. 36, No. (7), pp. 500–6), STN/CAS, Caplus, Abstract, 1990.*
Castillo et al., 'Synthesis and spectral properties of new complexes between glycine and titanium(III), vanadium(II), chromium(III), iron(III), cobalt(II), nickel(II) and copper(II)' (Transition Met. Chem. (Weinheim, Ger.)(1984), 9(7), 268–70), STN online, file.*
M'Hiri et al., 'Physicochemical and structural study of metal complexes of L–.beta.–phenylalanine' (J. Soc. Chim. Tunis. (1983), 9, 19–33), STN online, file CAPLUS, Abstract.*
Saxena et al., 'Electrometric study of divalent zinc, cadmium and mercury complexes of DL–tryptophan' (Trans. SAEST (1981), (1), 45–8), STN online, file CAPLUS, Abstract.*
Cusack et al. 'Synthesis, Moessbauer and infrared studies of inorganic tin derivatives of amino acids' (Inorg. Chim. Acta (1980), 46 (4), L73–L75), STN online, file HCAPLUS, Abstract.*
Mogilevkina et al., 'Antitumor activity of complexes of platinum with acids and peptides' (Onkologiya (Kiev) (1979), 14, 40–3), STN online, file HCAPLUS, Abstract.*
Volshtein et al., 'Complexes of platinum(II) with .beta.–phenyl–.alpha.–alanine' (Zh. Neorg. Khim. (1975), 20(12), 3352–6), STN online, file CAPLUS, Abstract.*

(List continued on next page.)

Primary Examiner—Jose' G. Dees
Assistant Examiner—Frank Choi
(74) Attorney, Agent, or Firm—Kilyk & Bowersox, P.L.L.C.

(57) ABSTRACT

Microbicidal formulations are described which are preferably ecologically friendly and non-toxic to mammals, and are highly effective against a broad spectrum of detrimental pathogenic microorganisms. The microbicidal formulation contains complexes having the formula R-M, wherein R is at least one organic chelating moiety and M is at least one metal ion which is microbicidal to at least one microorganism. These complexes can disrupt microorganism activities by penetrating the natural protecting bio-films of such microorganisms through the reaction of the R-group with the organic constituents of these microorganisms while releasing M into their intra-cellular media. Thus, this process exhibits its biocidal activities from the inside-out, contrary to other methods which rely on damaging the protective biofilms. These microbicidal formulations can be diluted in suitable proportions into aqueous systems to produce the desired dosages for each individual case, depending on the level and the severity of the contamination. The microbicidal formulations can be applied by conventional methods, e.g., spraying, soaking, fogging, impregnation, and the like.

30 Claims, No Drawings

OTHER PUBLICATIONS

Kollmann et al., 'Preparation and characterization of some amino acid and peptide complexes of gold (I,III), palladium (II), and platinum (II)' (J. Prakt. Chem. (1975), 317(3), 515–19), STN online, file HCAPLUS, Abstract.*

Natusch et al., 'Direct detection of mercury (II)–thio–ether bonding in complexes of methionine and S–methylcysteine by 1H nuclear magnetic resonance' (J. Chem. Soc. D (1970), (10), 596–7), STN online, file HCAPLUS, Abstract.*

Volshtein et al., 'Methionine as a tridentate ligand in platinum(II) complexes' (Dokl. Akad. Nauk SSSR (1968), 178(3), 595–7), STN online, file HCAPLUS, Abstract.*

Perrin et al., 'Histidine complexes with some bivalent cations' (J. Chem. Soc. A (1967), (5), 724–8), STN online, file HCAPLUS, Abstract.*

Sumarokova et al., 'Interaction of tin dichloride with organic bases' (Teor. Rastvorov (1971) 323–9), STN online, file CAPLUS, Abstract.*

Simeon et al., 'Chelation of some bivalent metal ions with alanine and phenylalanine' (Croat. Chem. Acta (1966), 38, 161–7), STN online, file HCAPLUS, Abstract.*

Khurshid, 'Antibacterial activity of iron(II) and zinc (II)–amino acid complexes' (Pak. J. Pharmacol. (1996), 13 (1), 41–45), STN online, file HCAPLUS, Abstract.*

Ali–Mohamed et al., 'Studies on the bacterial activity of cobalt(III) complexes. Part II. Cobalt (III) aminoacidato–complexes' (Transition Met. Chem. (London) (1989), 14 (3), 181–4), STN online, file HCAPLUS, Abstract.*

Kawada et al., 'Methionine and pentocystine copper salts as bactericides and fungicides' (1974, JP 49012028), STN online, file HCAPLUS, Abstract.*

Yoshida et al., 'Methionine zinc salt for the control of Alternaria mali' (1976, JP 51112517), STN online, file HCAPLUS, Abstract.*

Tumanov et al., 'Antimicrobial activity of copper (II) coordination compounds with .alpha.–amino acids' (Izv. Akad. Nauk Mold. SSR, Ser. Biol. Khim. Nauk (1983), (6), 44–6), STN online, file HCAPLUS, Abstract.

Ackermann et al., 'Preparation of substituted phenylalanine– metal complexes having fungicidal activity' (1989, DD 267731), STN online, file HCAPLUS, Abstract.

Jain et al., 'Some new metal chelates of L–lysine monohydrochloride as potential antifungals' (Indian J. Phys. Nat. Sci. (1983), 3(A), 51–2), STN online, file HCAPLUS, Abstract.

Yamashita et al., 'Antibacterial amino acids, inorganic salts thereof, and process for the preparation and use thereof' (1997), WO 9730057), STN online, file HCAPLUS, Abstract.

Van Nostrand's Scientific Encyclopedia (8th Ed. 1995), pp. 618, 619.*

Goodman and Gilman's, The Pharmacological Basis of Therapeutics (7th Ed. 1985), pp. 962, 963, 968.*

Simeon et al., 'Chelation of some bivalent metal ions with alanine and phenylalanine', Croatica Chemica Acta, vol. 38 (1966), pp. 161–167.*

Ohtaki et al., 'A potentiometric study on complex formation of silver(i) ion with glycine and beta–alanine in aqueous solution', Bull. Chem. Soc. Jpn., vol. 53 (1980), pp. 2865–2867.*

Gowda et al., 'Interaction of acidic amino acids with bivalent metal ions,' J. Electrochem. Soc. India., vol. 30, No. 4 (1981), pp. 336–340.*

* cited by examiner

MICROBICIDAL FORMULATIONS AND METHODS TO CONTROL MICROORGANISMS

The present invention relates in general to controlling microbicides and more particularly relates to microbicides which are preferably enviroinentally friendly and non-toxic to mammals and which are highly effective against viruses, amoebea, bacteria (both gram-negative and -positive), fungi, algae, spores, and the like.

BACKGROUND OF THE INVENTION

Water is the most important element of life since it comprises almost 80% of the human body. In addition, food hygiene depends solely on water, and therefore contamination of water is a common vehicle for the transport of epidemic diseases to humans like Typhoid, food poisoning, and Dysentery. For example, Psychrophilic bacteria whose presence in the micro-flora in water can affect refrigerated food and spoil it. Hence, water contamination cannot be overlooked and extreme measures should be taken to assure a high quality of water to sustain life.

With the advent of technology, clean water is becoming a scarce commodity. Water contamination is unequivocally becoming a worldwide problem with unknown ramifications, and billions of US dollars are spent annually to improve its quality. Contamination of waters is not only restricted to industrialized countries, but also to developing nations as well. Therefore, there is an immediate need to find poignant solutions to maintain and preserve water sources.

Recently, there has been a growing interest among scientists and engineers to develop new water and food disinfectant technologies to clean water from dangerous microorganisms. Various methods have been employed which are divided into two categories; namely, physical, chemical, or both. The physical category is represented by techniques utilizing ultrafiltration, reverse osmosis, radiation, freezing, heating, and ultrasound. Although these methods have proved to be effective, the drawbacks include the large electricity requirements and expensive equipment. On the other hand, the chemical category relies on the use of chemical adjuvants which exhibit biocidal properties such as aldehydes, phenols, alcohol, potassium penianganate, and chlorine and certain chlorine containing compounds. Some of these chemicals have many disadvantages associated with them and are now considered poisonous compounds. For instance, people coming into contact with these substances can develop skin irritation and suffer from long time illnesses which in some cases can be fatal; not to mention the unpleasant taste and odor associated with these chemicals. In addition, formation of mutagenic and carcinogenic agents, and genetic resistance are also some of their disadvantages. Notwithstanding, such compounds have afforded a way to battle these harmful microorganisms and their effectiveness have been unequivocally demonstrated.

Other methods have relied upon the use of ultra-violet irradiated silver fluoride solutions containing colloidal silver as a source of gennicide activities, such as U.S. Pat. No. 3,422,183, incorporated herein in its entirety by reference. However, such techniques require expensive equipment and large amounts of electricity.

Hydrogen peroxide is a highly oxidizing agent, and it has been used the past 40 years as a disinfectant. Its main advantage is that it does not produce toxic residue or by-products. It has been used ubiquitously as an indirect food additive, as a disinfectant in hospitals, as a decontamination and purification agent of industrial waste water, and as a cleaning agent for exhaust air. Nonetheless, it decomposes readily to form water and oxygen, and has high sensitivity to sunlight and UV rays. Therefore, it is not suited for long-term use since recontamination cannot be circumvented.

In 1880, the Swiss botanist Carl van Nageli observed that highly diluted silver solutions have an algicidal effects. To describe this effect he coined the term "Oligodynamic". Colloidal silver, which is a pure, all-natural substance consisting of sub-microscopic clusters of silver ions held in suspension in de-ionized water by tiny positive charges on the silver ions, is a powerful prophylactic antibiotic which was used for years with no known side effects. It acts as an inhibitor disabling particular enzymes which bacteria, fungi, and viruses used in their mode of metabolism.

Based on this oligodynamic property, U.S. Pat. No. 4,915,955, incorporated in its entirety herein by reference, combines the germicidal effects of hydrogen peroxide with colloidal silver, an inorganic acid and an organic stabilizer at concentrations of 10–35 mg/l against many forms of bacteria and viruses. The process is based on silver ions, with the aid of hydrogen peroxide, damaging the protective biofilms of these microorganisms. Hence, this method depends solely on killing germs intercellularly.

SUMMARY OF THE INVENTION

The present invention relies on using metal ions (M). A chemical matrix or complex is formed wherein these metal ions are attached to an organic-chelating moiety (R), to be used in stoichiometric amounts or more to form complexes, which serves as carriers for M into the intra-cellular medium of such microorganisms. These concentrated complexes can then be mixed with water to form suitable disinfectants. This process is different from previous methods found in the literature where the metal ion remains freely suspended in solution.

It is to be understood that the preceding general discussion and the discussion which follows are considered explanatory and exemplary in nature, and are solely intended to give additional merits of the current invention, as claimed.

DETAILED DESCRIPTION OF THE PRESENT INVENTION

The present invention provides a suitable concentrate of organo-metal compounds that form suitable disinfectants upon admixing with water or other aqueous sources. The basic principle that governs the formation of such a concentrate is the fact that the metal ions are attached to an organic-chelating R group used in stoichiometric amounts or more that forms organic complexes. These organic complexes can penetrate the protective biofilms of germs and other microorganisms. Once the R-M complex is inside the biofilm, it can then exhibit its genricidal or biocidal effects by releasing M into their intra-cellular media and, hence, disrupt microbial activities. In the most general terms, this scenario can be depicted as giving these germs a "poisonous pill." Thus, unlike other methods which attribute their biocidal effects through damaging the protective biofilms (from the outside-in, i.e., inter-cellularly), the present invention does the opposite; specifically, killing microorganisms from the inside-out, i.e., intra-cellularly.

To enhance its activity, the concentrated organic complex can be mixed with other disinfectants, including, but not limited to, isopropanol, chloroepoxide gluconate, chlorhexidine digluconate, chlorhexidine dihydrochloiide, chlorhexidine diacetate, and/or hydrogen peroxide, though it is not necessary. In addition, natural and artificial color and flavor additives can be added as well.

Of course, the microbicidal formulations of the present invention can be used either directly, by introduction to a system, e.g., a swimming pool, or can be diluted with aqueous solutions, like distilled and/or deionized water to provide the necessary biocidal activity, depending on the application.

With respect to the organic complex, R-M, the R group is an organic group which can complex with one or more metal ions, and is preferably a group which is amphoteric. Also, the R group is preferably of a chemical nature which microorganisms would find nurishable. Preferably, the R group is formed from at least one amino acid. The amino acids are preferably amphoteric, that is, they can react either as acids or as bases, depending on the circumstances. They exist primarily as neutral dipolar ions or zwitterions ($Z=H_3N^+$—CRH—$COO^-$). Hence, at low pH, the zwitterions exist as cations, and at high pH they exist as anions; therefore at a certain pH, the amino acids preferably exist primarily as zwitterions. This point is called the isoelectric point which depends on the structure of the given amino acid. Primary, secondary, or tertiary amines can all be used here as long as the amine is compatible with (M) in the formation of the complex. The amino acids are preferably chosen so as to make use of the lone pair of electrons on the nitrogen atom where the metal ions (the Lewis acid, electron pair acceptor) can form covalent bonds along with the carboxylic group. In essence, these metal ions, or Lewis acids, can share an electron pair donated by the amino acid, that is, the ligand, or Lewis base.

Preferably, examples of amino acid compounds which can be used to form the R group include, but are not limited to, α-amino acids. Specific examples include, but are not limited to, isoleucine, phenylalanine, leucine, lysine, methionine, threonine, tryptophan, valine, alanine, glycine, arginine, histidine, hydroxyproline, γ-aminobutyric acid, asparagine, aspartic acid, cysteine, glutamic acid, glutamine, pherylalanine, proline, serine, tyrosine, and derivatives thereof and mixtures thereof.

With respect to the other part of the complex which is M, M represents at least one metal ion which is microbicidal to at least one microorganism. Preferably, the metal ion is microbicidal to a multitude of microorganisms. Examples of the metal ion include, but are not limited to, silver, copper, zinc, mercury, manganese, chromium, nickel, cadmium, arsenic, cobalt, aluminum, lead, selenium, platinum, gold, titanium, tin, and the like. More than one type of R group and more than one type of M can be used to form the R-M complex, also, mixtures of different R-M complexes can also be used.

The complex of the present invention can be prepared by forming the metal ion from a metal salt compound and the organic chelating moiety from an organic compound which is preferably an amine, and more preferably an amino acid. In the preferred process of making the organic complex of the present invention, a metal salt compound is mixed with at least one inorganic acid preferably at room temperature and preferably in the presence of an aqueous solution like a distilled and deionized water. Then, at least an equimolar basis of the organic containing compound such as an amino acid is added to form the metal complex preferably while homogenizing the mixture. The resulting solution can then be further diluted with aqueous solution and preferably distilled and deionized water and further disinfectants or other additives can be added to form the microbicidal composition of the present invention.

According to the present invention, controlling the growth of at least one microorganism includes both the reduction and/or prevention of such growth. It is to be further understood that by "controlling," the growth of at least one microorganism is inhibited. In other words, there is no growth or substantially no growth of at least one microorganism. "Controlling" the growth of at least one microorganism includes maintaining a microorganism population at a desired level (including undetectable levels such as zero population), reducing a microorganism population to a desired level, and/or inhibiting or slowing the growth of at least one microorganism. Thus, materials and mediums susceptible to attack by at least one microorganism are preserved and/or protected from this attack and the resultant deleterious effects. The present invention also provides a method for controlling the growth of at least one microorganism in or on a material or medium susceptible to attack by the microorganism which comprises the step of adding to the material or medium a Composition of the present invention in an amount effective to control the growth of the microorganism.

The mode as well as the rates of application of the composition of this invention could vary depending upon the intended use. The composition could be applied by spraying or brushing onto the material or product. The material or product in question could also be treated by dipping in a suitable formulation of the composition. In a liquid or liquid-like medium, the composition could be added into the medium by pouring or by metering with a suitable device so that a solution or dispersion of the composition can be produced. Thus, the substrates or materials susceptible to attack by these types of microorganisms are preserved from this attack and the resulting spray or other detrimental effects caused by the microorganisms. Further, it is to be understood that "controlling" the growth of at least one microorganism also includes biostatically reducing and/or maintaining a low level of microorganisms such that the attack by microorganisms and any resulting spoilage or other detrimental effects are eliminated, i.e., the microorganism growth rate or microorganism attack rate is slowed down or eliminated.

Microorganisms, as used herein, include, but are not limited to bacteria, fungi, algae, viruses, amoebae, spores, and the like, and include both yeasts and molds.

Preferably, at least an equimolar portion of the chosen amino acid is used in preparing the solution, preferably in excess of the sequester univalent metal ions (e.g., Ag); at least twice as much for bivalent metals (e.g. Cu), and so on. Any source of ionic M in the form of salts can be used in the present invention. For the case of silver, colloidal silver can be used as well.

The present invention is further illustrated by the following examples. These experiments constitute some of the embodiments of the invention herein disclosed. After the preparation of these disinfectants according to the present technique, their efficacy with respect to toxicity was then tested and evaluated against a broad spectrum of pathogenic microorganisms.

METHODOLOGY

I. Chemical

Under minimum light, and at room temperature, a silver ion solution of $1.1 \times 10^5$ ppm was prepared by dissolving 400 mg of silver nitrate in 2.045 ml of double distilled-deionized water and 0.255 ml of 85% phosphoric acid. This solution was then used for the proceeding experiments.

EXAMPLE I

By using a micropipet, 230 μl of the above prepared solution was placed in a microtube where 34.61 mg of glutamic acid was added, and the mixture was stirred thoroughly. This amount of glutamic acid represents an equimolar amount of amino acid with respect to the silver ions in the above prepared solution. Instantly, an insoluble material was observed. This insoluble dispersant has microbial killing activities. This prepared solution was then mixed with 50 ml of double distilled-de-ionized water. The solution was mixed continuously until homogenization was achieved. Then, the product was poured into a dark bottle. This desired product can be added to or proportioned into aqueous systems and diluted to achieve the required germicidal potency, depending on its intended use.

EXAMPLE II

The same procedure above was duplicated, but the amino acid used was leucine instead of glutamic acid. The amount of leucine used in this case was 30.84 mg which again represents an equimolar amount of the acid with respect to the silver ions.

EXAMPLE III

The same procedure from Example I was again repeated, but the amino acid used was arginine. The amount of arginine used in this case was 40.97 mg which again represents an equimolar amount.

To study the effect of hydrogen peroxide on increasing the potency of these disinfectants, the three prepared solutions (Example I–III) were mixed with 50 ml of 50% $H_2O_2$ rather than water. Again, these prepared solutions were poured into dark bottles.

II. Biological

The above steps conclude the preparation of these disinfectants. However, to utilize these mixtures as bactericides, 5 ml of each bottled solution was added to 45 ml of double distilled-deionized water (10% by volume). Without the presence of $H_2O_2$, this constitutes an active concentration of about 51 ppm of complex silver which proved to be sufficient to readily kill bacteria. The upper and lower concentration limits may be different if desired, depending on the nature of the desired application. For the samples where $H_2O_2$ is present, the active concentration of the disinfectant should be around 56,000 ppm.

The diluted solutions were then tested on several kinds of actively growing pathogenic bacteria to ascertain their effectiveness. Different strains of pathogenic bacteria were employed for the testing; namely, E.coli, Stafelococus, Bascillus, and Salmonella. For all the bacteria used, the microbial killing activity was readily observed. The arginine-complex showed the most potency followed by the leucine-complex, and finally the glutamic acid-complex.

With respect to the presence of $H_2O_2$ in relation to its absence, the difference on the average was roughly around 3 times greater even though the active concentration was almost 1058 times greater than that for the case of an absence of $H_2O_2$. The difference in biocidal activity is not reflected in this value (1098 times greater while the increase is tripled). This is indicative that the biocidal activity is almost solely due to the R-M complex of the present invention. The order of efficacy with respect to the amino acid used was the same as when $H_2O_2$ was absent.

The biocides described herein have a plethora of applications and uses. They are suitable for the sterilization of drinking water, suitable for the beverage and food industry, suitable for sterilizing exposed surfaces, exhaust air and ventilation components, animal feed, suitable for use in the pharmaceutical industry, in hospitals, for surgical equipment, in swimming pools, in saunas, and for fish, poultry, and cattle fanning, and the like.

The previous explanation and the illustrations and procedures set forth above are solely intended for the purpose of setting out the generic and general embodiments of the present invention. Therefore, it is to be understood that the invention by no means is limited to the specific features disclosed herein, and such details can be varied by those skilled in the art in consideration of the present specification and practiced without departing from the true scope and merits of the invention.

Having thus described the present invention, the true scope and spirit of it is therefore presented by the following claims:

What is claimed is:

1. A microbicidal composition comprising a) a product obtained by combining under acidic conditions at least one metal salt compound and at least an equimolar amount of at least one amino acid in the presence of at least one inorganic acid at room temperature, wherein said metal salt compound has a metal which is microbicidal to at least one microorganism and b) at least one disinfectant, wherein b) is different from a).

2. The microbicidal composition of claim 1, wherein said at least one metal salt compound is a silver or copper or zinc salt compound.

3. The microbicidal composition of claim 1, wherein said at least one metal salt compound is a salt compound with the metal selected from copper, zinc, mercury, chromium, manganese, nickel, cadmium, arsenic, cobalt, aluminum, lead, selenium, platinum, gold, titanium, tin, or combinations thereof.

4. The microbicidal composition of claim 1, wherein said at least one amino acid is an alpha-amino acid.

5. The microbicidal composition of claim 1, wherein said at least one amino acid is isoleucine, phenylalanine, leucine, lysine, methionine, threonine, tryptophan, valine, alanine, glycine, arginine, histidine, or mixtures thereof.

6. The microbicidal composition of claim 1, wherein the molar ratio of metal salt compound to amino acid is from about 1:1 to about 2:1.

7. The microbicidal composition of claim 1, wherein an aqueous solution is added to the microbicidal composition.

8. The microbicidal composition of claim 7, wherein said microbicidal composition is present in said aqueous solution at a concentration of from about 0.001% to about 10% by total volume.

9. The microbicidal composition of claim 1, wherein said metal salt compound is a silver salt compound.

10. The microbicidal composition of claim 1, wherein said amino acid is isoleucine, phenylalanine, leucine, lysine, methionine, threonine, tryptophan, valine, alanine, glycine, arginine, histidine, asparagine, aspartic acid, cysteine, glutamic acid, glutamine, pherylalanine, proline, serine, tyrosine, or mixtures thereof, and wherein said at least one disinfectant comprises chlorhexidine gluconate, chlorhexidine digluconate, chlorhexidine dihydrochloride, chlorhexidine diacetate, isopropyl alcohol, hydrogen peroxide, or mixtures thereof.

11. The microbicidal composition of claim 1, wherein said at least one disinfectant comprises one or more of chlorhexidine gluconate, chlorhexidine digluconate, chlorhexidine dihydrochloride, and chlorhexidine diacetate.

12. The microbicidal composition of claim 1, wherein said at least one disinfectant comprises isopropyl alcohol, hydrogen peroxide, or both.

13. The microbicidal composition of claim 1, further comprising natural and artificial colors and flavors.

14. A method to control the growth of a microorganism susceptible to treatment with a metal, said method comprising:
   treating said microorganism with a microbicidal composition comprising a product obtained by combining under acidic conditions at least one metal salt compound and at least an equimolar amount of at least one amino acid in the presence of at least one inorganic acid at room temperature, wherein said metal salt compound has a metal which is microbicidal to at least one microorganism.

15. The method of claim 14, further comprising an aqueous solution.

16. The method of claim 14, wherein said at least one metal salt compound is a silver salt compound.

17. The method of claim 14, wherein said at least one metal salt compound is a salt compound wherein the metal is copper, zinc, mercury, chromium, manganese, nickel, cadmium, arsenic, cobalt, aluminum, lead, selenium, platinum, gold, titanium, tin, or combinations thereof.

18. The method of claim 14, wherein said amino acid is an alpha-amino acid.

19. The method of claim 14, wherein said amino acid is isoleucine, phenylalanine, leucirie, lysine, methionine, threonine, tryptophan, valine, alanine, glycine, arginine, histidine, or mixtures thereof.

20. The method of claim 14, wherein said amino acid is isoleucine, phenylalanine, leucine, lysine, methionine, threonine, tryptophan, valine, alanine, glycine, arginine, histidine, asparagine, aspartic acid, cysteine, glutamic acid, glutamine, proline, serine, tyrosine, or mixtures thereof, and wherein said at least one disinfectant comprises chlorhexidine gluconate, chlorhexidine digluconate, chlorhexidine dihydrochloride, chlorhexidine diacetate, isopropyl alcohol, hydrogen peroxide, or mixtures thereof.

21. A method of controlling biofouling in a system, comprising introducing to said system an effective amount of a microbicidal composition comprising a product obtained by combining under acidic conditions at least one metal salt compound and at least an equimolar amount of at least one amino acid in the presence of at least one inorganic acid at room temperature, wherein said metal salt compound has a metal which is microbicidal to at least one microorganism.

22. The microbicidal composition of claim 21, further comprising an aqueous solution.

23. The microbicidal composition of claim 22, wherein said microbicidal composition is present in said aqueous solution at a concentration of from about 0.001% to about 10% by total volume.

24. The microbicidal composition of claim 21, wherein said at least one metal salt compound is a silver salt compound.

25. The method of claim 21, wherein said at least one metal salt compound is a silver salt compound.

26. The method of claim 21, wherein said at least one metal salt compound is a salt compound wherein the metal is copper, zinc, mercury, chromium, manganese, nickel, cadmium, arsenic, cobalt, aluminum, lead, selenium, platinum, gold, titanium, tin, or combinations thereof.

27. The method of claim 21, wherein said amino acid is isoleucine, phenylalanine, leucine, lysine, methionine, threonine, tryptophan, valine, alanine, glycine, arginine, histidine, or mixtures thereof.

28. A method of controlling the growth of microorganisms comprising contacting the microorganisms with a microbicidal composition comprising a microbicidal composition comprising a product obtained by combining under acidic conditions a metal salt compound and at least an equimolar amount of at least one amino acid in the presence of at least one inorganic acid at room temperature, wherein said metal salt compound has a metal which is micrcobicidal to at least one microorganism.

29. The microbicidal composition of claim 28, wherein said at least one metal salt compound is a silver salt compound.

30. A method of controlling biofouling in a system, comprising introducing an effective amount of a) a microbicidal composition comprising a product obtained by combining under acidic conditions a metal salt compound and at least an equimolar amount of at least one amino acid in the presence of at least one inorganic acid at room temperature, wherein said metal salt compound has a metal which is microbicidal to at least one microorganism and b) at least one disinfectant to said system to control said biofouling, wherein b) is different from a).

* * * * *

UNITED STATES PATENT AND TRADEMARK OFFICE
CERTIFICATE OF CORRECTION

PATENT NO.     : 6,242,009 B1
DATED          : June 5, 2001
INVENTOR(S)    : Batarseh et al.

It is certified that error appears in the above-identified patent and that said Letters Patent is hereby corrected as shown below:

<u>Column 6,</u>
Line 55, delete "pherylalanine".

<u>Column 8,</u>
Lines 1, 3 and 7, "microbicidal composition" should read -- method --.

Signed and Sealed this

Twenty-fourth Day of December, 2002

JAMES E. ROGAN
*Director of the United States Patent and Trademark Office*